(12) United States Patent
Zehnder et al.

(10) Patent No.: US 8,075,598 B2
(45) Date of Patent: Dec. 13, 2011

(54) PEDICLE SCREW WITH A CLOSURE DEVICE

(75) Inventors: Thomas Zehnder, Bäch (CH); Reto Braunschweiler, Neftenbach (CH); Patrick White, West Chester, PA (US); Fabrice Chenaux, Exton, PA (US)

(73) Assignee: Spinelab AG, Zug (CH)

( * ) Notice: Subject to any disclaimer, the term of this patent is extended or adjusted under 35 U.S.C. 154(b) by 381 days.

(21) Appl. No.: 12/320,537

(22) Filed: Jan. 28, 2009

(65) Prior Publication Data
US 2009/0254128 A1 Oct. 8, 2009

(30) Foreign Application Priority Data
Jan. 28, 2008 (EP) .................................. 08101001

(51) Int. Cl.
*A61B 17/70* (2006.01)
(52) U.S. Cl. ...................................................... 606/265
(58) Field of Classification Search ........... 606/246–279
See application file for complete search history.

(56) References Cited

U.S. PATENT DOCUMENTS

| 5,667,508 | A | 9/1997 | Errico | |
|---|---|---|---|---|
| 6,652,526 | B1 * | 11/2003 | Arafiles | 606/308 |
| 7,819,901 | B2 * | 10/2010 | Yuan et al. | 606/264 |
| 2009/0036929 | A1 * | 2/2009 | Reglos et al. | 606/278 |
| 2009/0281573 | A1 * | 11/2009 | Biedermann et al. | 606/257 |

FOREIGN PATENT DOCUMENTS

| DE | 94 03 231 | 6/1994 |
|---|---|---|
| EP | 1759646 | 3/2007 |
| EP | 1815812 | 8/2007 |
| WO | 00/19923 | 4/2000 |

* cited by examiner

Primary Examiner — Bruce E Snow
(74) Attorney, Agent, or Firm — Jacobson Holman PLLC

(57) ABSTRACT

A pedicle screw with a closure device (16) for securing a rod (10) for stabilization of the vertebral column comprises a screw-in part (2), a head part (3) provided on the screw-in part (2), and a U-shaped recess (4) disposed in the head part (3), which recess is formed by the inner surfaces (5, 6) of two arms (7, 8) and a bottom surface (9) connecting the two inner surfaces. The rod (10) is insertable into this recess, and is held by the closure device (16). The rod (10) is provided with ridges (12) and grooves (13) running transversely with respect to the rod axis (11). Likewise provided with corresponding ridges (14) and grooves (15) is the bottom surface (9). The closure device (16) comprises a support element (17), which is insertable between the two arms (7, 8). Disposed in a displaceable way on the support element (17) are two sliding parts (20, 21), which, via a movement mechanism, are able to be brought from a position of being pushed against each other into a position of being pushed apart, in which pushed-apart position the two end regions (29), remote from one another, of the two sliding parts (20, 21) each project into a recess (23, 24) of the two arms (7, 8) in the state of the support element (17) being inserted in the screw. The closure device (16) is thereby locked with the pedicle screw; the rod (10) is firmly held in the pedicle screw.

10 Claims, 5 Drawing Sheets

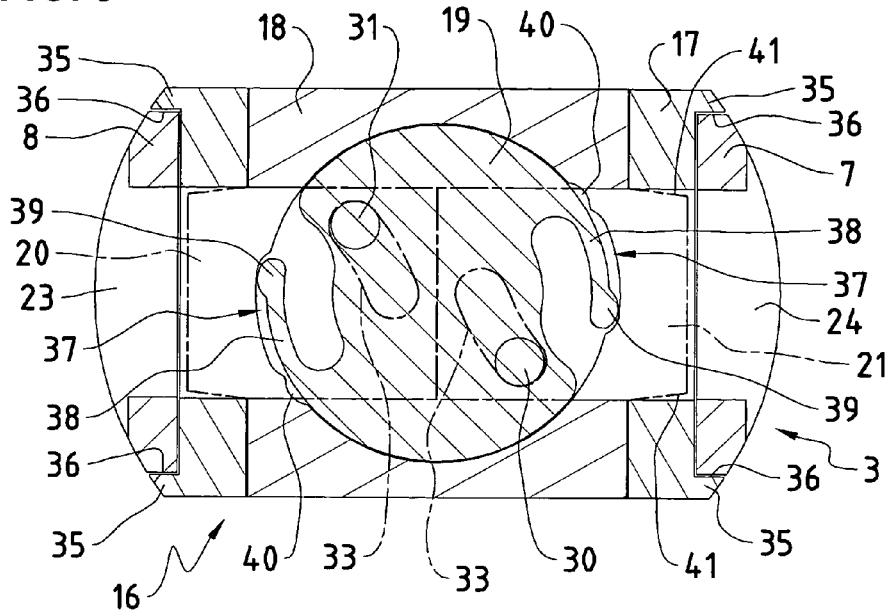

PEDICLE SCREW WITH A CLOSURE DEVICE

Figure 1:
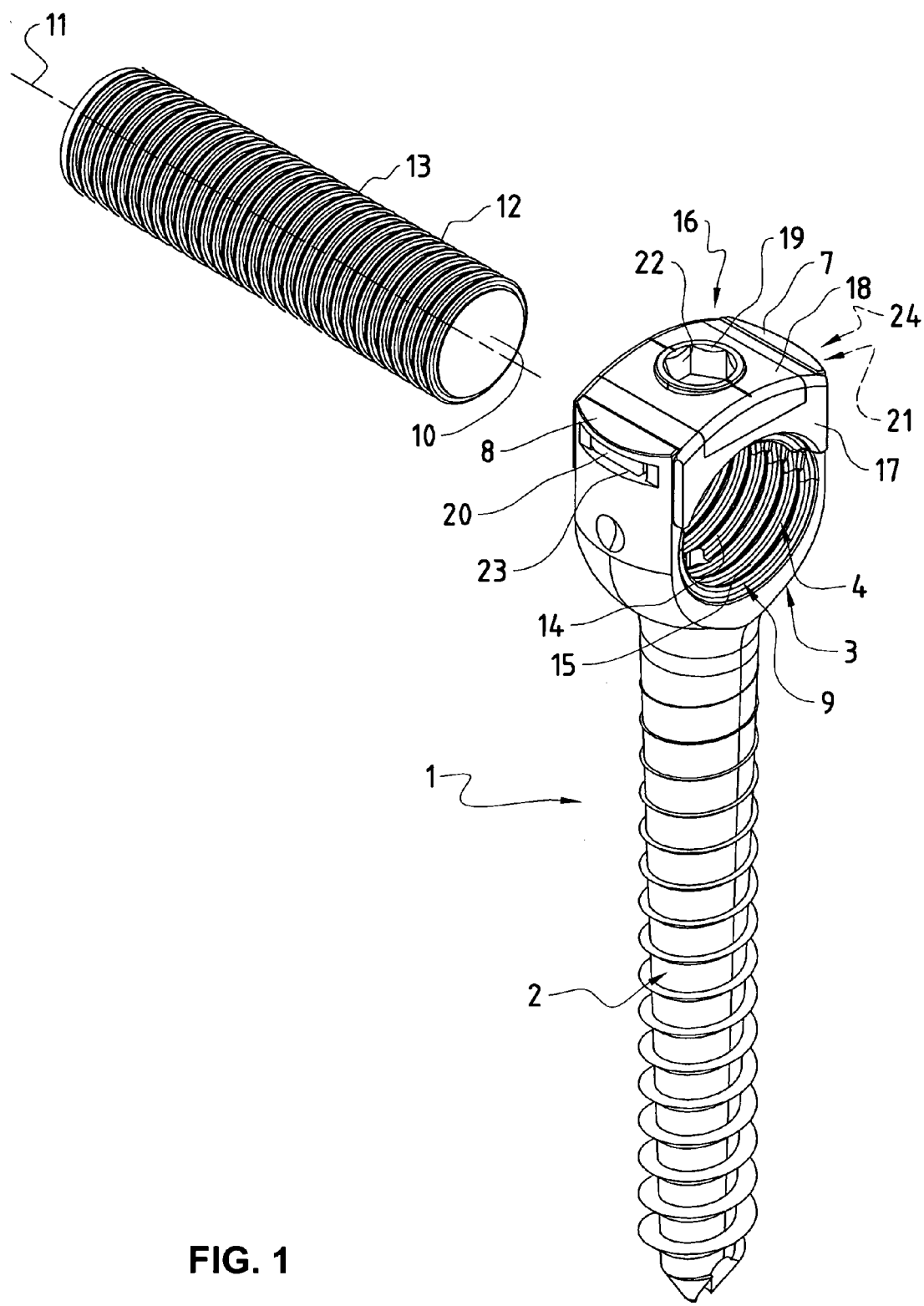

This invention relates to a pedicle screw with a closure device for securing a rod for stabilization of the vertebral column, comprising a screw-in part, a head part provided on the screw-in part, a U-shaped recess disposed in the head part, which recess is formed by the inner surfaces of two arms and a bottom surface connecting the two inner surfaces, in which recess the rod is insertable and is held by the closure device, which rod is provided with ridges and grooves running substantially transversely with respect to the rod axis and which bottom surface is provided with corresponding ridges and grooves.

Pedicle screws of this kind with a closure device for securing a rod are known from the state of the art in diverse designs. These screws serve to stabilize the vertebral column of patients who have severely damaged vertebral columns. For stabilization of these vertebral columns, one pedicle screw each is screwed into a number of vertebral bodies, and a rod is placed in the head parts of these pedicle screws, which rod is then connected in each case to the respective pedicle screw, closure devices being used for this purpose. Two different forms of stabilization can be achieved with such pedicle screws and inserted rod, depending upon which type of rod is used. With use of a rigid rod, a stiffening of the affected vertebral bodies is achieved. For a supportive stabilization of the vertebral bodies, an elastic rod can be used; thereby achieved is that a certain flexibility is allowed between the individual vertebral bodies.

Regardless of which system is used, an optimal connection between inserted rod and pedicle screw is to be aimed for, which is supposed to be achieved through the closure devices used.

Known from EP-B-1 119 304 is a device for securing spinal rods, which device consists of a pedicle screw having a head portion with a U-shaped recess, in which the rod to be secured is inserted. Serving as closure device is a rotatable element with two laterally projecting camming surfaces opposite each other, which have a helical inclination. By turning of this rotational element, these camming surfaces end up in corresponding slot-shaped recesses of the two arms of the U-shaped recess. By turning this rotational element, the rod is held in a clamped way. In order to be able to prevent a release of this rotational element, the clamping surface facing the rod is provided with transversely running recesses which are supposed to engage in the surface of the rod upon reaching of the clamping position.

This device is simple to operate. It may not be unproblematic, however, with the predetermined positions of the recesses which are supposed to engage in the rod, to obtain the right tensional force so that the rod is clamped firmly in the pedicle screw in an optimal way.

Also known are devices in which a formfitting connection is obtained between the pedicle screw and the rod, in that the entry in the pedicle screw for the rod and the rod itself are provided in each case with corresponding ridges and grooves that run transversely to the rod direction, and engage in one another. With these devices it is not absolutely necessary for the rod to be held in the pedicle screw by a clamping force; it can suffice for the pedicle screw to be closed with a closure device which is provided with a click-in device which is provided with click-in elements that engage in corresponding recesses of the pedicle screw in the closed state, and the rod is correspondingly held.

Such devices are very easy to handle. In practical application, however, checked very carefully must be whether the corresponding click-in elements are completely engaged in the respective recesses of the pedicle screw.

The object of the present invention is thus to create a pedicle screw with a closure device for securing a rod for stabilization of the vertebral column, which is easy to handle and with which it is ensured that, in the closed state, the connection between closure device and pedicle screw is optimal.

This object is achieved according to the invention in that the closure device comprises a support element, which is insertable between the two arms, in that two sliding parts are disposed in a displaceable way on the support element, which sliding parts are able to be brought, via a movement mechanism, from a position of being pushed against each other into a position of being pushed apart, in which pushed-apart position the two end regions, remote from each other, of the two sliding parts project into one recess each of the two arms in the state of the support element being inserted between the arms, and the closure device is locked with the pedicle screw.

By actuating the movement mechanism during closing of the closure device for securing a rod in a pedicle screw, the two sliding parts are led in a compulsory way into the two recesses on the pedicle screw; a secure locking is thereby ensured.

The movement mechanism preferably consists of a rotatable part, which is disposed in the support element in a way rotatable about an axis perpendicular to the direction of displacement of the two sliding parts, which rotatable part is provided with two pins aligned parallel to the axis, which pins each co-operate with a cam device provided on each sliding part.

The sliding parts and the rotatable part are inserted in the support element, a cover is placed on the support element and is connected to the latter, which cover is provided with a bore in which the rotatable part is rotatably borne, whereby achieved in an advantageous way is that the closure device is constructed as a unit that can be easily handled.

Another preferred embodiment of the invention consists in that disposed between rotatable part and support element are engagement elements, which keep the two sliding parts in an engaged state in the pushed-apart position. On the one hand, through the engagement of the engagement elements, it is indicated to the person inserting the closure device into the pedicle screw that the closure device is optimally inserted in the pedicle screw. On the other hand, the position of the two sliding parts located in the pushed-apart state is secured; an autonomous displacement of these two sliding parts is thereby prevented.

The engagement elements are preferably each made up of a resilient arm, the one end of which is attached to the rotatable part, and on the resilient free end of which a protrusion is provided which, in the engaged state, engages in each case in a corresponding recess provided on the support element or on the cover, respectively. Besides optimal functioning, a simple and compact construction is also thereby achieved.

To actuate the rotatable part, this part is provided with a contoured cavity into which a turning tool having a correspondingly contoured shape can be inserted.

The end regions remote from each other of the sliding parts are preferably provided with bevels, whereby a trouble-free movement of the two sliding parts in the two recesses of the two arms of the pedicle screw is ensured.

The surface of the support element turned toward the rod preferably has a shape adapted to the rod surface, and this surface is provided with corresponding ridges and grooves, whereby an optimal securing of the rod in the pedicle screw is achievable.

The support element is preferably provided with guide ribs at its corner regions by means of which the support element is placeable in a guided way on the head part, which is provided with guide surfaces. Placement of the closure device on the pedicle screw is thereby simplified.

Another preferred embodiment of the invention consists in the rod being made of an elastic material, in particular a polyurethane-based biocompatible plastic, whereby a supportive stabilization of the vertebral body is achieved.

An embodiment of the invention will be explained more closely in the following, by way of example, with reference to the attached drawing.

Figure 2:
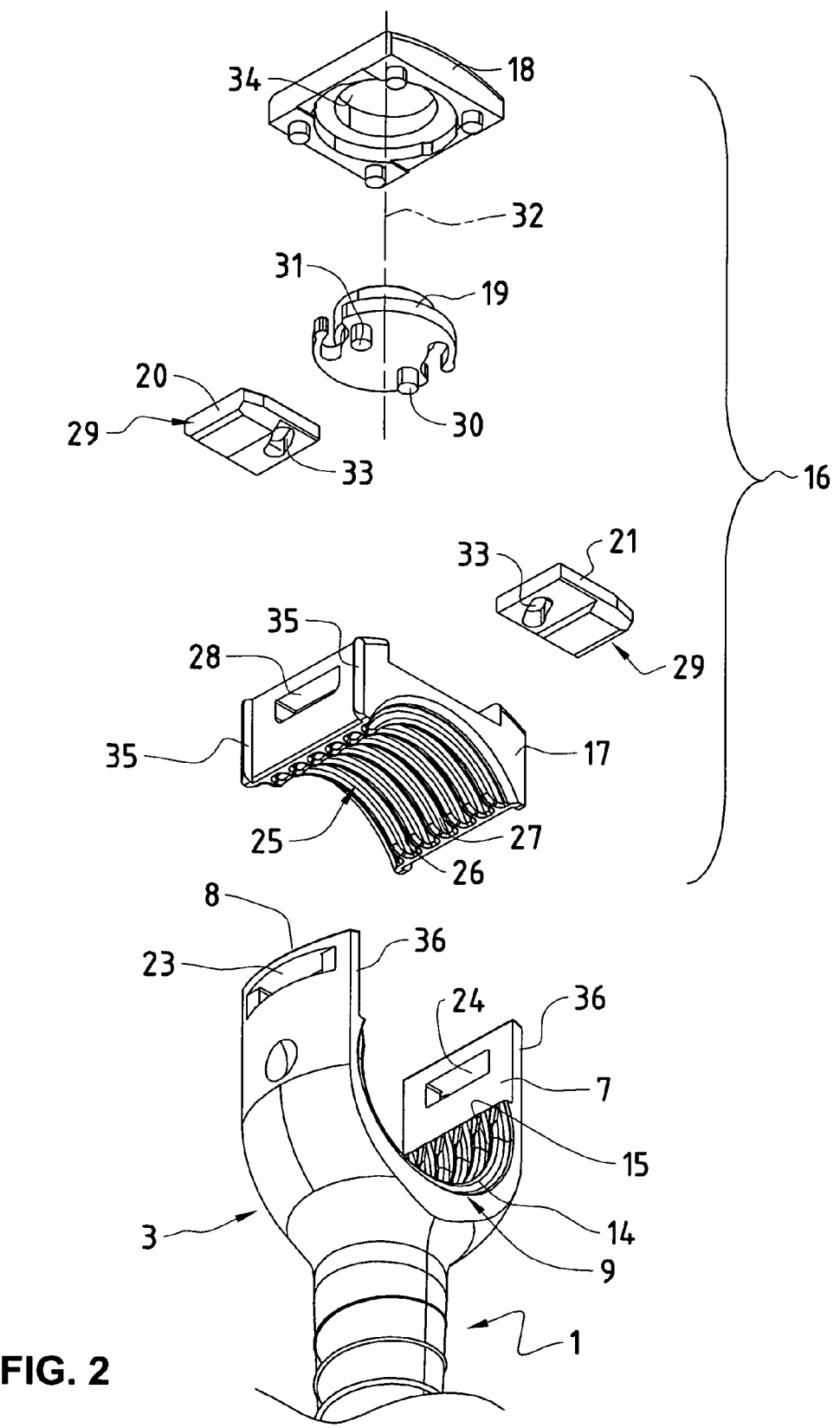
Figure 3:
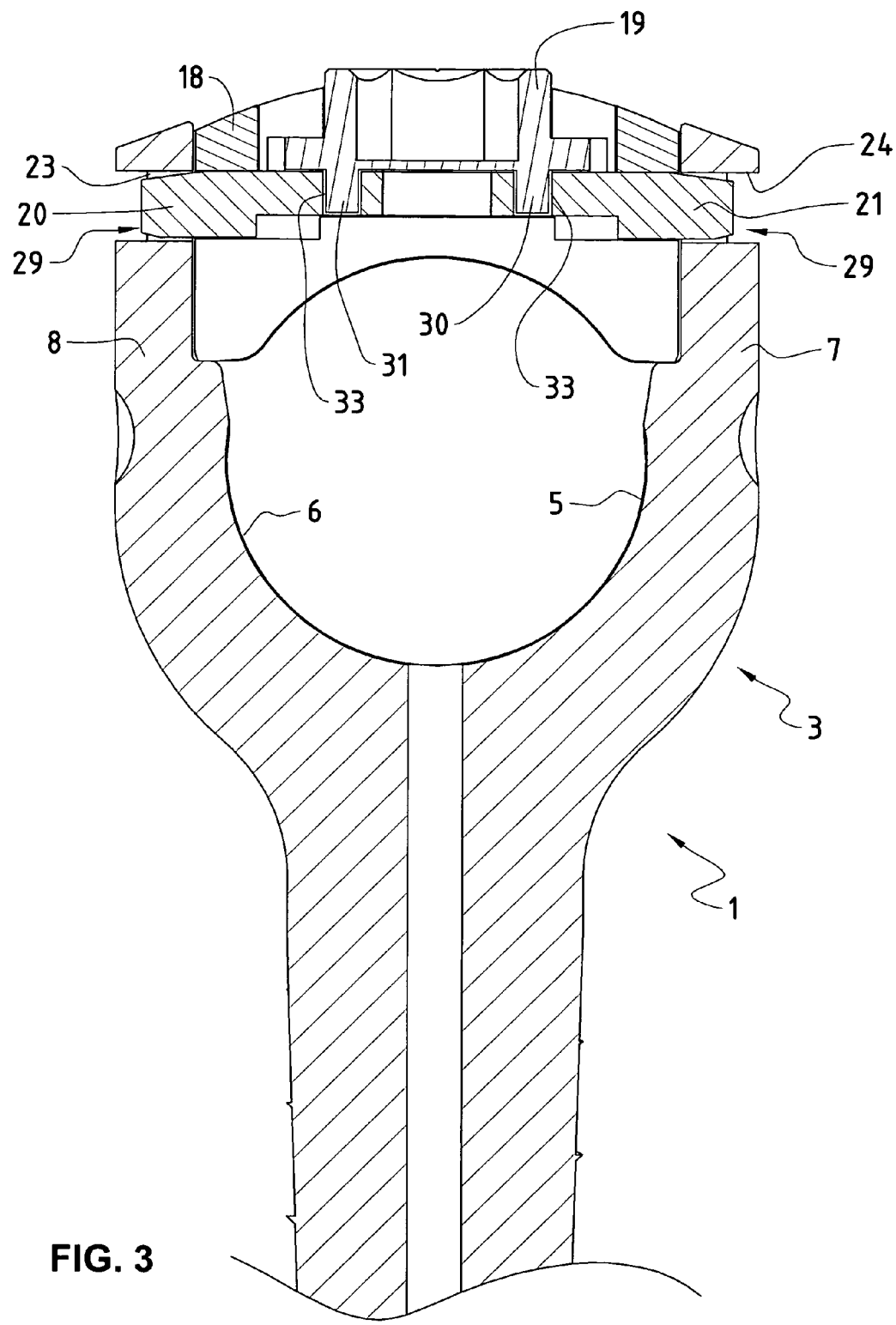
Figure 4:
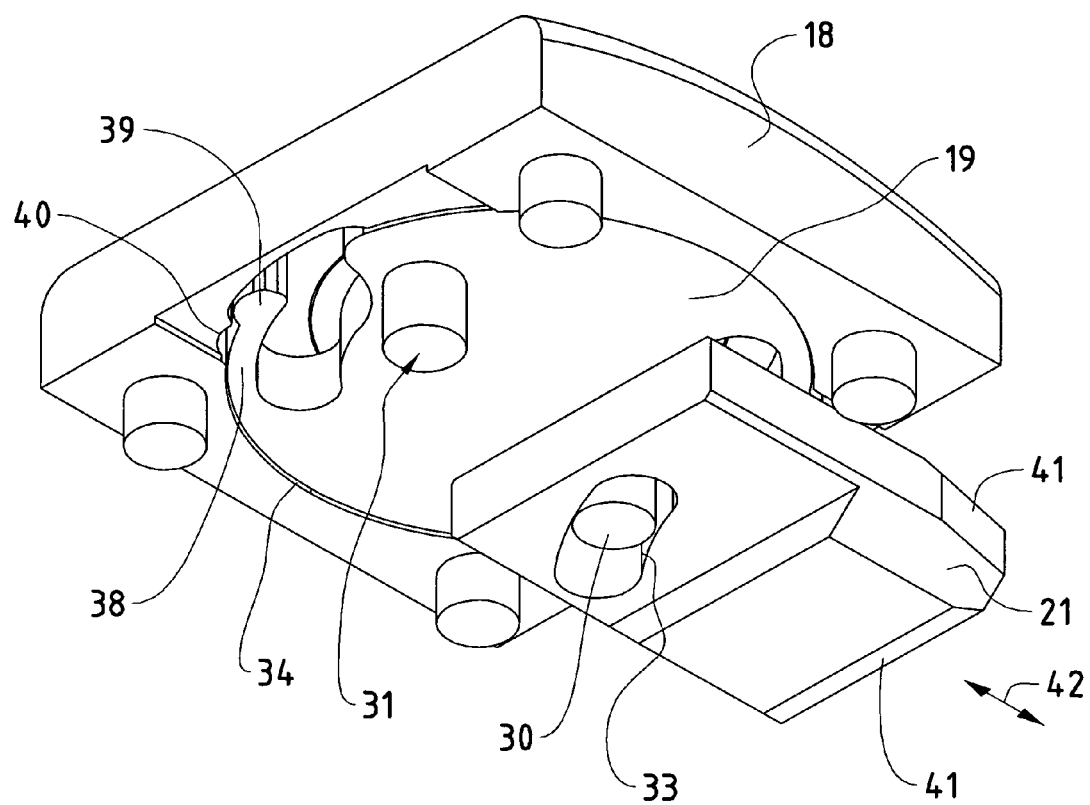

Shown are:

FIG. 1, in a three-dimensional representation, a pedicle screw with a closure device placed thereon with a rod;

FIG. 2, in a three-dimensional representation, the head part of the pedicle screw and the individual elements of the closure device in disassembled state;

FIG. 3, a sectional drawing through the pedicle screw with closure device put on, in locked position;

FIG. 4, in a three-dimensional representation, a view of the support element of the closure device with rotatable part put on and one of the two sliding parts;

FIG. 5, a view from above, in section, of the closure device with the two sliding parts in the pushed together position; and FIG. 6, a view from above, in section, of the closure device with sliding parts pushed apart and engaged engagement elements.

As can be seen from FIG. 1, the pedicle screw 1 consists of a screw-in part 2 provided with a threading, with which screw-in part the pedicle screw 1 is able to be screwed into a vertebral body of a vertebral column of a patient in a known way. Disposed on this screw-in part 2 is a head part 3, which is provided with a U-shaped recess 4. This U-shaped recess is formed by the inner surfaces 5, 6 (FIG. 3) of two arms 7, 8, which are firmly attached to the screw-in part 2. The two inner surfaces 5 and 6 of these two arms are connected together through a bottom surface 9, which bottom surface 9 is adapted to the shape of the rod 10 to be inserted into this U-shaped recess 4, which rod is shown outside the pedicle screw 1 in FIG. 1.

This rod 10 is provided with ridges 12 and grooves 13 running transversely to the rod axis 11. The bottom surface 9 of the U-shaped recess 4 is likewise provided with ridges 14 and grooves 15, corresponding to the ridges 12 and grooves 13 of the rod 10. In the state of the rod 10 being inserted in the U-shaped recess 4, the ridges 12 of the rod 10 are situated in the corresponding grooves 15 of the U-shaped recess 4, while the ridges 14 of the U-shaped recess 4 penetrate into the grooves 13 of the rod 10. A formfitting connection is thereby obtained. A shift of the rod 10 with respect to the pedicle screw 1 in the direction of the rod axis 11 is not possible.

Placed on the pedicle screw 1 shown in FIG. 1 is a closure device 16. This closure device 16 consists of a plurality of individual components assembled into a unit, namely a support element 17, a cover 18, a rotatable part 19 and two sliding parts 20 and 21. These components will still be described in detail later on. Via the rotatable part 19, the two sliding parts 20 and 21 allow themselves to be slid, whereby the closure device 16 is able to be locked in the state of being placed on the pedicle screw 1, and the rod inserted in the pedicle screw 1 is thereby held in an optimal way. For operation of the rotatable part 19, this part is provided with a structured or fluted cavity 22 into which a known turning tool having a correspondingly structured or fluted shape is able to be inserted, whereby the closure device 16 is able to be brought from the unlocked state into the locked state and vice versa by turning this turning tool. The two arms 7 and 8 of the head part 3 of the pedicle screw 1 are each provided with a recess 23, 24 for receiving the two sliding parts 20 and 21.

FIG. 2 shows the head part 3 of the pedicle screw 1, with the two arms 7 and 8, which are connected to each other through the bottom surface 9, which bottom surface 9 is provided with the corresponding ridges 14 and grooves 15. Provided in the two arms 7 and 8 are the two recesses 23 and 24, into which recesses the two sliding parts 20 or respectively 21 are able to be inserted.

The support element 17 is provided with a surface 25 which, in the state of the closure device 16 being placed on the pedicle screw 1, is turned toward the rod 10 inserted in the pedicle screw, as can be seen from FIG. 1. This surface 25 has a shape adapted to the rod surface. It is also provided with ridges 26 and grooves 27, which correspond to the ridges 14 and the grooves 15 of the bottom surface 9 of the head part, and align therewith, so that the ridges 12 and the grooves 13 of the rod 10 are completely enclosed by the head part 3 and the closure device 16, whereby an optimal formfitting securing of the rod 10 in this pedicle screw 1 is achieved.

In the support element 17, the two sliding parts 20 and 21 are able to be inserted in corresponding guides (not shown). For this purpose, the support element 17 is provided with an opening 28 on both sides. The two sliding parts 20 and 21 thus allow themselves to be slid along these guides (not shown) toward each other and away from each other, whereby, in the pushed-apart state, these two sliding parts 20, 21 project through the openings 28 by the two end regions 20 remote from each other and protrude.

Placed on the two sliding parts 20 and 21 displaceably inserted in the support element 17 is the rotatable part 19. On the surface turned toward the two sliding parts 20 and 21, this rotatable part 19 is provided with two pins 30 and 31 each, which are aligned parallel to the axis 32, about which axis 32 the rotatable part 19 is rotatable. The two pins 30 and 31 each project into a cam device 33 provided on each sliding part 20, 21, which cam device 33 is designed as a slot-shaped recess made in the respective sliding part 20 or respectively 21.

Placed on the rotatable part 19 is the cover 18, which is provided with a bore 34, in which the rotatable part 19 is rotatably borne. The cover 18 is able to be firmly attached in a known way to the support element 17, for example via press pin or in another known, suitable way. The closure device 16 constructed in this way is able to be placed on the pedicle screw 1 with the rod inserted in the pedicle screw, as is shown in FIG. 1. For this purpose, the support element has a guide rib 35 in each case in its corner regions by means of which the support element 17 and thus the closure device 16 are placeable in a guided way on the head part 3, the head part 3 being correspondingly provided with guide surfaces 36.

Shown in assembled state in FIG. 4 is the cover 18, the rotatable part 19 inserted therein and one of the two sliding parts 21, whereby the cooperation is made clear. By turning the rotatable part 19 in the cover 18, the sliding part 21 is displaced in the direction of the arrow 42, via the pin 30 and the cam device 33 provided in the sliding part 21. The sliding part 20 (not shown) is correspondingly shifted, also in the direction of the arrow 42, via the pin 31. Thereby achieved is a displacement of the two sliding parts 20 and 21 from a position of being pushed against each other into a pushed-apart position.

FIG. 3 shows the closure device 16, which is placed on the pedicle screw 1. By turning of the rotatable part 19, after the placement of the closure device 16 on the head part 3 of the pedicle screw 1, the two sliding parts 20 and 21 are moved into the pushed-apart position via the pins 30 and 31 provided on the rotatable part 19 and the cam devices 33 in the two sliding parts 20 and 21. The end regions 29, remote from each other, of the two sliding parts 20 and 21 were thereby pushed into the recesses 23 and 24 provided on each respective arm 7 or respectively 8 of the head part 3 of the pedicle screw 1. The closure device 16 is thereby locked in the head part 3 of the pedicle screw 1; a rod inserted in the head part 3 of the pedicle screw 1 would thus be held in a formfitting way.

FIG. 5 shows the two sliding parts 20 and 21 in the pushed together position. This means that, in this position, the closure device 16 is able to be placed on the head part 3 of the pedicle screw. The guide ribs 35 are hereby guided by the guide surfaces 36 of the two arms 7 and 8. The two sliding parts 20 and 21 are thus pulled back far enough that they are able to move in between the two arms 7 and 8.

The rotatable part 19 is provided with engagement elements 37. These engagement elements 37 each consist of a resilient arm 38, one end of which is attached to the rotatable part 19. Provided on the resilient free end of each resilient arm 38 is a protrusion 39.

When the closure device 16 is placed on the head part 3, the sliding parts 20 and 21 are situated at the height of the recesses 23 and 24 provided on the two arms 7 and 8 of the head part 3. By turning of the rotatable part 19, the two sliding parts 20 and 21 are brought into the pushed-apart position, which is carried out by the sliding of the two pins 30 and 31 in the cam devices 33, as can be seen from FIG. 6. Thus the closure device 16 is situated in the locked position with respect to the head part 3. In this position, the two protrusions 39 of the resilient arms 38 end up in a recess 40 provided in the cover 18, and snap in here. In this rotational position of the rotatable part 19, this part is thereby held in this position, and an autonomous, undesired turning back of the rotatable part 19 is prevented. The locked position of the closure device 16 with respect to the head part 3 is thereby ensured. This engagement step also allows the person operating the closure device to note that the lock-in position has been reached, whereby it is indicated that the closure device is locked in an optimal way. As can be seen in particular also in FIG. 4, it is ensured by means of the bevels 41 provided on the sliding parts 20 and 21 that the movement of the sliding parts 20 and 21 into the respective recess 23 or 24 of the two arms 7 and 8 is possible in an optimal way. Also visible in FIG. 4 is one of the two resilient arms 38 with the protrusion 39, which is attached to the rotatable part 19, as well as the recess 40 provided in the bore 34 of the cover 18, in which the protrusion 39 can engage.

Achieved with this closure device for the correspondingly equipped pedicle screw is a very easy handling during insertion and securing of the rod. Also achieved is that the rod is optimally held in the pedicle screw in a formfitting way. Through the engagement elements it is also ensured that the closure device cannot become loose of its own accord. The pedicle screw and the closure device are preferably made of a titanium alloy.

The invention claimed is:

1. A pedicle screw with a closure device for securing a rod for stabilization of the vertebral column, comprising a screw-in part, a head part provided on the screw-in part, a U-shaped recess disposed in the head part, which recess is formed by the inner surfaces of two arms and a bottom surface connecting the two inner surfaces, in which recess the rod is insertable and is held by the closure device, which rod is provided with ridges and grooves running substantially transversely with respect to the rod axis, and which bottom surface is provided with corresponding ridges and grooves, wherein the closure device comprises a support element, which is insertable between the two arms, in that two sliding parts are disposed in a displaceable way on the support element, which sliding parts are able to be brought, via a movement mechanism, from a position of being pushed against each other into a position of being pushed apart, in which pushed-apart position, two end regions, remote from each other, of the two sliding parts each project into a recess of the two arms in the state of the support element being inserted between the arms, and the closure device is locked with the pedicle screw.

2. The pedicle screw with a closure device according to claim 1, wherein the movement mechanism consists of a rotatable part, which is disposed in the support element in a way rotatable about an axis perpendicular to the direction of displacement of the two sliding parts, which rotatable part is provided with two pins aligned parallel to the axis, which pins each co-operate with a cam device provided on each sliding part.

3. The pedicle screw with a closure device according to claim 2, wherein the sliding parts and the rotatable part are inserted in the support element, and in that a cover is placed on the support element and is connected to the latter, which cover is provided with a bore in which the rotatable part is rotatably borne.

4. The pedicle screw with a closure device according to claim 2, wherein disposed between rotatable part and support element are engagement elements, which keep the two sliding parts in an engaged state in the pushed-apart position.

5. The pedicle screw with a closure device according to claim 4, wherein the engagement elements are each made up of a resilient arm the one end of which is attached to the rotatable part, and on the resilient free end of which a protrusion is provided which, in the engaged state, engages in each case in a corresponding recess provided on the support element or respectively on the cover.

6. The pedicle screw with a closure device according to claim 2, wherein the rotatable part is provided with a contoured cavity, into which a turning tool having a correspondingly contoured shape is insertable.

7. The pedicle screw with a closure device according to claim 1, wherein the end regions, remote from each other, of the sliding parts are provided with bevels.

8. The pedicle screw with a closure device according to claim 1, wherein the surface of the support element turned toward the rod has a shape adapted to the rod surface, and in that this surface is provided with corresponding ridges and grooves.

9. The pedicle screw with a closure device according to claim 1, wherein the support element is provided with guide ribs at its corner regions by means of which the support element is placeable in a guided way on the head part, which is provided with guide surfaces.

10. The pedicle screw with a closure device according to claim 1, wherein the rod is made of an elastic material, in particular a polyurethane-based biocompatible plastic.

* * * * *